US007767638B2

(12) United States Patent
Singh et al.

(10) Patent No.: US 7,767,638 B2
(45) Date of Patent: Aug. 3, 2010

(54) AZEOTROPE-LIKE COMPOSITIONS OF TETRAFLUOROPROPENE AND HYDROFLUOROCARBONS

(75) Inventors: Rajiv R. Singh, Getzville, NY (US); Hang T. Pham, Amherst, NY (US); Gary Knopeck, Lakeview, NY (US); David J. Williams, East Amherst, NY (US)

(73) Assignee: Honeywell International Inc., Morristown, NJ (US)

( * ) Notice: Subject to any disclaimer, the term of this patent is extended or adjusted under 35 U.S.C. 154(b) by 1086 days.

(21) Appl. No.: 11/119,053

(22) Filed: Apr. 29, 2005

(65) Prior Publication Data

US 2005/0247905 A1 Nov. 10, 2005

Related U.S. Application Data

(63) Continuation-in-part of application No. 10/837,526, filed on Apr. 29, 2004, now Pat. No. 7,524,805.

(51) Int. Cl.
*C09K 5/04* (2006.01)

(52) U.S. Cl. ....................... 510/408; 510/412; 510/415; 252/67; 252/68

(58) Field of Classification Search ................. 510/408, 510/412, 415; 252/67, 68
See application file for complete search history.

(56) References Cited

U.S. PATENT DOCUMENTS

| | | | | |
|---|---|---|---|---|
| 2,834,748 | A | 5/1958 | Bailey et al. | 260/42 |
| 2,846,458 | A | 8/1958 | Haluska | 260/448.2 |
| 2,889,379 | A | 6/1959 | Ruh et al. | 260/653.4 |
| 2,917,480 | A | 12/1959 | Bailey et al. | 260/42 |
| 3,384,828 | A | 5/1968 | Pierre et al. | 328/155 |
| 3,723,318 | A | 3/1973 | Butler | 252/67 |
| 4,465,786 | A | 8/1984 | Zimmer et al. | 502/169 |
| 4,798,818 | A | 1/1989 | Baizer et al. | 502/228 |
| 5,182,040 | A | 1/1993 | Bartlett et al. | 252/67 |
| 5,648,017 | A | 7/1997 | Bartlett et al. | 252/67 |
| 5,714,083 | A | 2/1998 | Turner | 252/68 |
| 6,111,150 | A | 8/2000 | Sakyu et al. | 570/167 |
| 6,858,571 | B2 * | 2/2005 | Pham et al. | 510/408 |
| 2004/0119047 | A1 * | 6/2004 | Singh et al. | 252/71 |
| 2005/0233931 | A1 * | 10/2005 | Singh et al. | 510/408 |

FOREIGN PATENT DOCUMENTS

| | | |
|---|---|---|
| EP | 0398 147 | 11/1990 |
| EP | 974 571 | 1/2000 |

* cited by examiner

*Primary Examiner*—Gregory E Webb
(74) *Attorney, Agent, or Firm*—Colleen D. Szuch

(57) ABSTRACT

Provided are azeotrope-like compositions comprising tetrafluoropropene and hydrofluorocarbons and uses thereof, including use in refrigerant compositions, refrigeration systems, blowing agent compositions, and aerosol propellants.

27 Claims, No Drawings

AZEOTROPE-LIKE COMPOSITIONS OF TETRAFLUOROPROPENE AND HYDROFLUOROCARBONS

The present application is a Continuation-in-Part of U.S. application Ser. No. 10/837,526 filed on Apr. 29, 2004 (now U.S. Pat. No. 7,524,805).

The present application is also related to and incorporates by reference each of the following United States Patent Applications: U.S. application Ser. No. 10/837,525, filed Apr. 29, 2004; Ser. No. 10/837,521, filed Apr. 29, 2004, Ser. No. 10/694,273, filed Oct. 27, 2003; Ser. No. 10/695,212, filed Oct. 27, 2003; Ser. No. 10/694,272 filed Oct. 27, 2003.

The present application is related to and incorporates by reference each of the following U.S. Provisional Applications: 60/567,426; 60/567,429; 60/567,427; 60/567,425 and 60/567,428, all of which were filed on Apr. 29, 2004.

FIELD OF INVENTION

The present invention relates generally to compositions comprising 1,1,3,3-tetrafluoropropene. More specifically, the present invention provides azeotrope-like compositions comprising 1,1,1,3-tetrafluoropropene and uses thereof.

BACKGROUND

Fluorocarbon based fluids have found widespread use in industry in a number of applications, including as refrigerants, aerosol propellants, blowing agents, heat transfer media, and gaseous dielectrics. Because of the suspected environmental problems associated with the use of some of these fluids, including the relatively high global warming potentials associated therewith, it is desirable to use fluids having low or even zero ozone depletion potential, such as hydrofluorocarbons ("HFCs"). Thus, the use of fluids that do not contain chlorofluorocarbons ("CFCs") or hydrochlorofluorocarbons ("HCFCs") is desirable. Furthermore, some HFC fluids may have relatively high global warming potentials associated therewith, and it is desirable to use hydrofluorocarbon or other fluorinated fluids having global warming potentials as low as possible while maintaining the desired performance in use properties. Additionally, the use of single component fluids or azeotrope-like mixtures, which do not substantially fractionate on boiling and evaporation, is desirable. However, the identification of new, environmentally-safe, non-fractionating mixtures is complicated due to the fact that azeotrope formation is not readily predictable.

The industry is continually seeking new fluorocarbon based mixtures that offer alternatives, and are considered environmentally safer substitutes for CFCs and HCFCs. Of particular interest are mixtures containing both hydrofluorocarbons and other fluorinated compounds, both of low ozone depletion potentials. Such mixtures and their uses are the subject of this invention.

DESCRIPTION OF PREFERRED EMBODIMENTS

The present inventors have developed several compositions that help to satisfy the continuing need for alternatives to CFCs and HCFCs. According to certain embodiments, the present invention provides azeotrope-like compositions comprising, or consisting essentially of, 1,1,1,3-tetrafluoropropene ("HFO-1234ze"), preferably trans-1,1,1,3-tetrafluoropropene ("transHFO-1234ze") and at least one compound component selected from the group consisting of 1,1-difluoroethane ("HFC-152a"), 1,1,1,2,3,3,3-heptafluoropropane ("HFC-227ea"), 1,1,1,2,-tetraafluoethane ("HFC-134a"), 1,1,1,2,2-pentafluoroethane ("HFC-125") and combinations of two or more of these. Thus, the present invention overcomes the aforementioned shortcomings by providing azeotrope-like compositions that are, in preferred embodiments, substantially free of CFCs and HCFCs and which exhibit relatively constant boiling point and vapor pressure characteristics.

The preferred compositions of the invention tend to exhibit characteristics which make them particularly desirable for use in a number of applications, including as refrigerants in automotive air conditioning and heat pump systems, and in stationary air conditioning and refrigeration. In particular, applicants have recognized that the present compositions tend to exhibit relatively low global warming potentials ("GWPs"), preferably less than about 1000, more preferably less than about 500, and even more preferably less than about 150. Preferred embodiments of the present compositions tend also to have similar or higher refrigeration capacity than many conventional HFC refrigerants, for example, HFC-134a. Accordingly, applicants have recognized that such compositions can be used to great advantage in a number of applications, including as replacements for CFCs such as dichlorodifluormethane (CFC-12), HCFCs, such as chlorodifluoromethane (HCFC-22), and HFCs, such as tetrafluoroethane (HFC-134a) and combinations of HFCs and CFCs, such as the combination of CFC-12 and 1,1-difluorethane (HFC-152a) (the combination CFC-12:HFC-152a in a 73.8:26.2 mass ratio being known as R-500) in refrigerant, aerosol, and other applications.

Additionally, applicants have recognized surprisingly that the azeotrope-like compositions of the present invention exist and can be readily formed in view of the teachings contained herein. Accordingly, one aspect of the present invention provides methods of producing azeotrope-like compositions comprising the step of combining HFO-1234, preferably HFO-1234ze, and even more preferably transHFO-1234ze, and a compound selected from the group consisting of 1,1-difluoroethane ("HFC-152a"), 1,1,1,2,3,3,3-heptafluoropropane ("HFC-227ea"), 1,1,1,2,-tetraafluoethane ("HFC-134a"), 1,1,1,2,2-pentafluoroethane ("HFC-125") and combinations of two or more of these, in amounts effective to produce an azeotrope-like composition.

The term "HFO-1234" is used herein to refer to all tetrafluoropropenes. Among the tetrafluoropropenes are included HFO-1234yf and both cis- and trans-1,3,3,3-tetrafluoropropene (HFO-1234ze). The term HFO-1234ze is used herein generically to refer to 1,3,3,3-tetrafluoropropene, independent of whether it is the cis- or trans-form. The terms "cisHFO-1234ze" and "transHFO-1234ze" are used herein to describe the cis- and trans- forms of 1,3,3,3-tetrafluoropropene respectively. The term "HFO-1234ze" therefore includes within its scope cisHFO-1234ze, transHFO-1234ze, and all combinations and mixtures of these.

Although the properties of cisHFO-1234ze and transHFO-1234ze differ in at least some respects, and while the present azeotrope-like compositions are based mainly on transHFO-1234ze, it is contemplated that the cisHFO-1234ze form may be present in certain embodiments in amounts which do not negate the essential nature of the azeotrope-like composition. Accordingly, it is to be understood that the terms "HFO-1234ze" and 1,3,3,3-tetrafluoropropene refer to both stereo isomers, and the use of this term is intended to indicate that each of the cis-and trans-forms applies and/or is useful for the stated purpose unless otherwise indicated.

HFO-1234 compounds are known materials and are listed in Chemical Abstracts databases. The production of fluoropropenes such as CF3CH═CH2 by catalytic vapor phase fluorination of various saturated and unsaturated halogen-containing C3 compounds is described in U.S. Pat. Nos. 2,889,379; 4,798,818 and 4,465,786, each of which is incorporated herein by reference. EP 974,571, also incorporated herein by reference, discloses the preparation of 1,1,1,3-tetrafluoropropene by contacting 1,1,1,3,3-pentafluoropropane (HFC-245fa) in the vapor phase with a chromium-based catalyst at elevated temperature, or in the liquid phase with an alcoholic solution of KOH, NaOH, Ca(OH)2 or Mg(OH)2. In addition, methods for producing compounds in accordance with the present invention are described generally in connection with pending United States Patent Application Ser. No. 11/757,782 entitled "Process for Producing Fluoropropenes", which is also incorporated herein by reference.

In addition, applicants have recognized that the azeotrope-like compositions of the present invention exhibit properties that make them advantageous for use as, or in, numerous applications, including as heat transfer compositions (including as refrigerants in automotive air conditioning and heat pump systems, and in stationary air conditioning, heat pump and refrigeration systems), blowing agents, propellants and sterilizing agents. Accordingly, yet other aspects of the present invention provide one or more azeotrope-like compositions of the present invention and methods associated with these and other uses.

In another embodiment, the compositions of this invention may be used as propellants in sprayable compositions, either alone or in combination with known propellants. The propellant compositions comprise, more preferably consists essentially of, and, even more preferably consist of the compositions of the invention. The active ingredient to be sprayed together with inert ingredients, solvents, and other materials may also be present in the sprayable mixture. Preferably, the sprayable composition is an aerosol. Suitable active materials to be sprayed include, without limitation, cosmetic materials such as deodorants, perfumes, hair sprays, cleaning solvents, lubricants, as well as medicinal materials such as anti-asthma medications.

The present compositions find particular advantage in methods and systems involving aerosol compositions, particularly in medicinal compositions, cleaning composition, and other sprayable compositions. Those of skill in the art will be readily able to adapt the present compositions for use in such applications without undue experimentation.

Azeotrope-like Compositions

As used herein, the term "azeotrope-like" is intended in its broad sense to include both compositions that are strictly azeotropic and compositions that behave like azeotropic mixtures. From fundamental principles, the thermodynamic state of a fluid is defined by pressure, temperature, liquid composition, and vapor composition. An azeotropic mixture is a system of two or more components in which the liquid composition and vapor composition are equal at the stated pressure and temperature. In practice, this means that the components of an azeotropic mixture are constant-boiling and cannot be separated during a phase change.

Azeotrope-like compositions are constant boiling or essentially constant boiling. In other words, for azeotrope-like compositions, the composition of the vapor formed during boiling or evaporation is identical, or substantially identical, to the original liquid composition. Thus, with boiling or evaporation, the liquid composition changes, if at all, only to a minimal or negligible extent. This is to be contrasted with non-azeotrope-like compositions in which, during boiling or evaporation, the liquid composition changes to a substantial degree. All azeotrope-like compositions of the invention within the indicated ranges as well as certain compositions outside these ranges are azeotrope-like.

The azeotrope-like compositions of the invention may include additional components that do not form new azeotrope-like systems, or additional components that are not in the first distillation cut. The first distillation cut is the first cut taken after the distillation column displays steady state operation under total reflux conditions. One way to determine whether the addition of a component forms a new azeotrope-like system so as to be outside of this invention is to distill a sample of the composition with the component under conditions that would be expected to separate a non-azeotropic mixture into its separate components. If the mixture containing the additional component is non-azeotrope-like, the additional component will fractionate from the azeotrope-like components. If the mixture is azeotrope-like, some finite amount of a first distillation cut will be obtained that contains all of the mixture components that is constant boiling or behaves as a single substance.

It follows from this that another characteristic of azeotrope-like compositions is that there is a range of compositions containing the same components in varying proportions that are azeotrope-like or constant boiling. All such compositions are intended to be covered by the terms "azeotrope-like" and "constant boiling". As an example, it is well known that at differing pressures, the composition of a given azeotrope will vary at least slightly, as does the boiling point of the composition. Thus, an azeotrope of A and B represents a unique type of relationship, but with a variable composition depending on temperature and/or pressure. It follows that, for azeotrope-like compositions, there is a range of compositions containing the same components in varying proportions that are azeotrope-like. All such compositions are intended to be covered by the term azeotrope-like as used herein.

It is well-recognized in the art that it is not possible to predict the formation of azeotropes. (See, for example, U.S. Pat. No. 5,648,017 (column 3, lines 64-65) and U.S. Pat. No. 5,182,040 (column 3, lines 62-63), both of which are incorporated herein by reference). Applicants have discovered unexpectedly that HFO-1234 and HFCs, particularly the HFCs described above, form azeotrope-like compositions.

According to certain preferred embodiments, the azeotrope-like compositions of the present invention comprise, and preferably consist essentially of, effective amounts of HFO-1234 and the above-noted HFCs. The term "effective amounts" as used herein refers to the amount of each component which upon combination with the other component, results in the formation of an azeotrope-like composition of the present invention.

The azeotrope-like compositions of the present invention can be produced by combining effective amounts of HFO-1234 and a component, preferably in fluid form, selected from the group consisting of 1,1-difluoroethane ("HFC-152a"), 1,1,1,2,3,3,3-heptafluoropropane ("HFC-227ea"), 1,1,1,2,-tetrafluroethane ("HFC-134a"), 1,1,1,2,2-pentafluoroethane ("HFC-125") and combinations of two or more of these. Any of a wide variety of methods known in the art for combining two or more components to form a composition can be adapted for use in the present methods to produce an azeotrope-like composition. For example, transHFO-1234ze and HFC-152a can be mixed, blended, or otherwise combined by hand and/or by machine, as part of a batch or continuous reaction and/or process, or via combinations of two or more such steps. In light of the disclosure herein, those of skill in the art will be readily able to prepare azeotrope-like compositions according to the present invention without undue experimentation.

Preferably, such azeotrope-like compositions comprise, preferably consist essentially of, from greater than zero to about 99 wt. % of HFO-1234, preferably transHFO-1234ze, and from about 1 wt. % to less than 100 wt. % of one or more components selected from the group consisting 1,1-difluoroethane ("HFC-152a"), 1,1,1,2,3,3,3-heptafluoropropane ("HFC-227ea"), 1,1,1,2,-tetrafluroethane ("HFC-134a"), and 1,1,1,2,2-pentafluoroethane ("HFC-125"). It will be appreciated by those skilled in the art that the production transHFO-1234ze will commonly result in product which includes a small proportion of compound which are not transHFO-1234ze. For example, it would be common in expected for a product designated as transHFO-1234ze to include a minor percentage, for example about 0.5 wt. % up to about 1 wt. % of other components, including particularly cisHFO-1234ze and/or HFO-1234yf. The term "consisting essentially of transHFO-1234ze" used herein is intended to generally include such compositions.

More preferably, the present azeotrope-like compositions comprise, and preferably consist essentially of, from about 5 wt. % to about 90 wt. % of HFO-1234, preferably transHFO-1234ze, and from about 10 wt. % to about 90 wt. % of one or more components selected from the group consisting of 1,1-difluoroethane ("HFC-152a"), 1,1,1,2,3,3,3-heptafluoropropane ("HFC-227ea"), 1,1,1,2,-tetrafluroethane ("HFC-134a"), and 1,1,1,2,2-pentafluoroethane ("HFC-125"). Other preferred compositions comprise, or consist essentially of, greater than zero to about 60 wt. % of HFO-1234, preferably transHFO-1234ze, and from about 40 wt. % to less than 100 wt. % of one or more components selected from the group consisting 1,1 -difluoroethane ("HFC-152a"), 1,1,1,2,3,3,3-heptafluoropropane ("HFC-227ea"), 1,1,1,2,-tetrafluroethane ("HFC-134a"), and 1,1,1,2,2-pentafluoroethane ("HFC-125"). Unless otherwise indicated, all weight percents reported herein are based on the total weight of the HFO-1234 and the one or more components selected from the indicated group in the azeotrope-like composition.

According to certain preferred embodiments, the present transHFO-1234ze azeotrope-like compositions have a boiling point of from about −15° C. to about −50° C., and even more preferably from about −28° C. to about −50° C., at about 14 psia. In certain preferred embodiments, the present compositions have a boiling point of about −23° C. ±2° C. In other preferred embodiments, the present compositions have a boiling point of about −18° C. ±1° C. Additionally, in other preferred embodiments the present compositions have a boiling point of about −47° C. ±2° C. Preferably, the HFO-1234 containing compositions of the present invention are substantially homogenous azeotrope-like compositions.

HFO-1.234/HFC-134a

Certain preferred embodiments of the present invention provide azeotrope-like compositions comprising transHFO-1234ze and HFC-134a. Preferably, the novel azeotrope-like compositions of the present invention comprise effective amounts of transHFO-1234ze and HFO-134a. These embodiments preferably provide azeotrope-like compositions comprising, and preferably consisting essentially of, from greater than zero to about 75 weight percent transHFO-1234ze and from about 25 wt. % to less than 100 wt. % HFC-134a, more preferably from greater than zero to about 60 wt. % transHFO-1234ze and from about 40 wt. % to less than 100 wt. % HFO-134a, and even more preferably from about 1% to about 40 weight percent transHFO-1234ze and from about 60 wt. % to about 99 wt. % HFC-134a. In certain preferred embodiments, the azeotrope-like compositions comprise, and preferably consist essentially of, from about 5 wt. % to about 35 wt % transHFO-1234ze and from about 65 wt. % to about 95 wt. % HFO-134a.

Preferably, the HFO-1234/HFC-134a compositions of the present invention have a boiling of from about −26° C. to about −23° C. at about 14 psia.

Preferably, the HFO-1234/HFO-134a compositions of the present invention have a boiling of about −25° C. ±3° C. at about 14 psia. In certain embodiments, the compositions have a boiling point of preferably about −25° C. ±2° C., and even more preferably −25° C. ±1° C., all measured at about 14 psia.

Preferably the HFO-1234 of these embodiments is transHFO-1234ze.

HFO-1234/HFC-125

In certain other preferred embodiments, the present invention provides azeotrope-like compositions comprising transHFO-1234ze and HFC-125. Preferably, such novel azeotrope-like compositions of the present invention comprise, or consist essentially of, effective amounts of transHFO-1234ze and HFC-125. These embodiments preferably provide azeotrope-like compositions comprising, and preferably consisting essentially of, from greater than zero to about 99 weight percent transHFO-1234ze and from about 1 wt. % to less than 100 wt. % HFC-125, more preferably from greater than zero to about 75 wt. % transHFO-1234ze and from about 25 wt. % to less than 100 wt. % HFC-125, even more preferably from about greater than zero to about 60 wt. % tansHFO-1234ze and from about 40 to less than 100 wt. % HFC-125, and even more preferably from about 1% to about 40 weight percent transHFO-1234ze and from about 60 wt. % to about 99 wt. % HFC-125. In certain preferred embodiments, the azeotrope-like compositions comprise, and preferably consist essentially of, from about 2 wt. % to about 15 wt % transHFO-1234ze and from about 85 wt. % to about 98 wt. % HFO-125.

Other preferred compositions comprise, or consist essentially of, from greater than zero to about 45 wt. % transHFO-1234ze and from about 55 to less than 100 wt. % HFC-125.

Preferably, the HFO-1234/HFC-125 compositions of the present invention have a boiling of about −44° C. to about −50° C., at about 14 psia.

Preferably the HFO-1234/HFC-125 compositions of the present invention have a boiling of about −47° C. ±2° C., preferably −47° C. ±1° C. at about 14 psia.

HFO-1234/HFC-152a

In certain other preferred embodiments, the present invention provides azeotrope-like compositions comprising transHFO-1234ze and HFC-152a. Preferably, such novel azeotrope-like compositions of the present invention comprise, or consist essentially of, effective amounts of transHFO-1234ze and HFC-152a. These embodiments preferably provide azeotrope-like compositions comprising, and preferably consisting essentially of, from greater than zero to about 99 weight percent transHFO-1234ze and from about 1 wt. % to less than 100 wt. % HFC-152a, more preferably from greater than zero to about 50 wt. % transHFO-1234ze and from about 50 wt. % to less than 100 wt. % HFC-152a, and even more preferably from about greater than zero to about 40 wt. % transHFO-1234ze and from about 60% to less than 100 wt. % HFC-227ea. In certan preferred embodiments, the azeotrope-like compositions comprise, and preferably consist essentially of, from about 15 wt. % to about 30 wt % transHFO-1234ze and from about 70 wt. % to about 85 wt. % HFO-152a.

Preferably, the HFO-1234/HFC-152a compositions of the present invention have a boiling of from about −22° C. to about −24° C. at about 14 psia.

Preferably, the HFO-1234/HFO-152a compositions of the present invention have a boiling of about −23° C. ±2° C. at about 14 psia. In certain embodiments, the compositions have a boiling point of preferably about −23° C. ±1° C. measured at about 14 psia.

Preferably the HFO-1234 of these embodiments is transHFO-1234ze.

HFO-1234/HFC-227ea

Certain preferred embodiments of the present invention provide azeotrope-like compositions comprising transHFO-1234ze and HFC-227ea. Preferably, the novel azeotrope-like compositions of the present invention comprise effective amounts of transHFO-1234ze and HFO-227ea. These embodiments preferably provide azeotrope-like compositions comprising, and preferably consisting essentially of, from greater than zero to about 75 weight percent HFC-227ea and from about 25 wt. % to less than 100 wt. % transHFO-1234ze, more preferably from greater than zero to about 60 wt. % HFC-227ea and from about 40 wt. % to less than 100 wt. % transHFC-1234ze, and even more preferably from about 1% to about 40 weight percent HFC-227ea and from about 60 wt. % to about 99 wt. % transHFO-1234ze. In certain preferred embodiments, the azeotrope-like compositions comprise, and preferably consist essentially of, from about 5 wt. % to about 35 wt % HFC-227ea and from about 65 wt. % to about 95 wt. % transHFO-1234ze.

Preferably, the HFO-1234/HFC-227ea compositions of the present invention have a boiling of from about −17° C. to about −19° C. at about 14 psia.

Preferably, the HFO-1234/HFO-227ea compositions of the present invention have a boiling of about −18° C. ±2° C. at about 14 psia, and even more preferably about −18° C. ±1° C., measured at about 14 psia.

Preferably the HFO-1234 of these embodiments is transHFO-1234ze.

Composition Additives

The azeotrope-like compositions of the present invention may further include any of a variety of optional additives including lubricants, stabilizers, metal passivators, corrosion inhibitors, flammability suppressants, and the like.

According to certain embodiments, the azeotrope-like compositions of the present invention further comprise a stabilizer. Any of a variety of compounds suitable for stabilizing an azeotrope-like composition of the present invention may be used. Examples of certain preferred stabilizers include stabilizer compositions comprising stabilizing diene-based compounds, and/or phenol compounds, and/or epoxides selected from the group consisting of aromatic epoxides, alkyl epoxides, alkenyl epoxides, and combinations of two or more thereof.

In certain preferred embodiments, the compositions of the present invention further comprise a lubricant. Any of a variety of conventional and unconventional lubricants may be used in the compositions of the present invention. An important requirement for the lubricant is that, when in use in a refrigerant system, there must be sufficient lubricant returning to the compressor of the system such that the compressor is lubricated. Thus, suitability of a lubricant for any given system is determined partly by the refrigerant/lubricant characteristics and partly by the characteristics of the system in which it is intended to be used. Examples of suitable lubricants include, which are generally those commonly used in refrigeration machinery using or designed to use hydrofluorocarbon (HFC) refrigerants, chloroflurocarbon refrigerants and hydrochlorofluorocarbons refrigerants, include mineral oil, silicone oil, polyalkyl benzenes (sometimes referred to as (PABs), polyol esters (sometimes referred to as (POEs), polyalkylene glycols (sometimes referred to as (PAGs), polyalkylene glycol esters (sometimes referred to as PAG esters), polyvinyl ethers (sometimes referred to as PVEs), poly(alpha-olefin) (sometimes referred to as PAOs) and halocarbon oils, particularly poly(chlorotrifluorethylene) and the like. Mineral oil, which comprises paraffin oil or naphthenic oil, is commercially available. Commercially available mineral oils include Witco LP 250 (registered trademark) from Witco, Zerol 300 (registered trademark) from Shrieve Chemical, Sunisco 3GS from Witco, and Calumet R015 from Calumet. Commercially available polyalkyl benzene lubricants include Zerol 150 (registered trademark). Commercially available esters include neopentyl glycol dipelargonate which is available as Emery 2917 (registered trademark) and Hatcol 2370 (registered trademark). Commercially available PAGs include Motorcraft PAG Refrigerant Compressor Oil, available from Ford, with similar products being available from Dow. Commercially available PAOs include CP-4600 from CPI Engineering. Commercially available PVEs are available from Idemitsu Kosan. Commercially available PAG esters are available from Chrysler. Other useful esters include phosphate esters, dibasic acid esters, and fluoroesters.

For refrigeration systems using or designed to use HFCs, it is generally preferred to use as lubricants PAGs, PAG esters, PVEs, and POEs, particularly for systems comprising compression refrigeration, air-conditioning (especially for automotive air conditioning) and heat pumps. For refrigeration systems using or designed to use CFCs or HCFCs, it is generally preferred to use as lubricants mineral oil or PAB. In certain preferred embodiments, the lubricants of this invention are organic compounds which are comprised of carbon, hydrogen and oxygen with a ratio of oxygen to carbon and are included to provide, in combination with the amounts used, effective solubility and/or miscibility with the refrigerant to ensure sufficient return of the lubricant to the compressor. This solubility or miscibility preferably exists at at least one temperature from about −30° C. and 70° C.

PAGs and PAG esters are highly preferred in certain embodiments because they are currently in use in particular applications such as original equipment mobile air-conditioning systems. Polyol esters are highly preferred in other certain embodiments because they are currently in use in particular non-mobile applications such as residential, commercial, and industrial air conditioning and refrigeration. Of course, different mixtures of different types of lubricants may be used.

Uses of the Compositions

The present compositions have utility in a wide range of applications. For example, one embodiment of the present invention relates to heat transfer compositions, such as refrigerant compositions, comprising an azeotrope-like composition of the present invention. The heat transfer compositions of the present invention are generally adaptable for use in heat transfer applications, that is, as a heating and/or cooling medium. Although it is contemplated that the compositions of the present invention may include the present azeotrope-like composition in combination with one or more other compounds or combinations of compounds in widely ranging amounts, it is generally preferred that heat transfer compositions of the present invention, including refrigerant compositions, consist essentially of, and in some embodiments consist of the present azeotrope-like compositions.

The heat transfer compositions of the present invention may be used in any of a wide variety of refrigeration systems including air-conditioning (including both stationary and mobile air conditioning systems), refrigeration, heat-pump systems, and the like. In certain preferred embodiments, the compositions of the present invention are used in refrigeration systems originally designed for use with an HFC-refrigerant, such as, for example, HFC-134a or an HCFC refrigerant, such as, for example, HCFC-22. The preferred compositions of the present invention tend to exhibit many of the desirable characteristics of HFC-134a and other HFC-refrigerants, including non-flammability, and a GWP that is as low, or lower than that of conventional HFC-refrigerants and a capacity that is as substantially similar to or substantially matches, and preferably is as high as or higher than such refrigerants. In particular, applicants have recognized that the present compositions tend to exhibit relatively low global warming potentials ("GWPs"), preferably less than about 1000, more preferably less than about 500, and even more preferably less than about 150. In addition, the relatively constant boiling nature of the compositions of the present invention makes them even more desirable than certain conventional HFCs, such as R-404A or combinations of HFC-32, HFC-125 and HFC-134a (the combination HFC-32:HFC-125:HFC134a in approximate 23:25:52 weight ratio is referred to as R-407C), for use as refrigerants in many applications. Heat transfer compositions of the present invention are particularly preferred as replacements for HFC-134, HFC-152a, HFC-22, R-12 and R-500. The present compositions are also believed to be suitable as replacements for the above noted compositions in other applications, such as aerosols, blowing agents and the like.

In certain other preferred embodiments, the present compositions are used in heat transfer systems in general, and in refrigeration systems in particular, originally designed for use with a CFC-refrigerant. Preferred refrigeration compositions of the present invention may be used in refrigeration systems containing a lubricant used conventionally with CFC-refrigerants, such as mineral oils, polyalkylbenzene, polyalkylene glycols, and the like, or may be used with other lubricants traditionally used with HFC refrigerants.

As used herein the term "refrigeration system" refers generally to any system or apparatus, or any part or portion of such a system or apparatus, which employs a refrigerant to provide cooling. Such refrigeration systems include, for example, air conditioners, electric refrigerators, chillers (including chillers using centrifugal compressors), transport refrigeration systems, commercial refrigeration systems and the like.

In certain embodiments, the compositions of the present invention may be used to retrofit refrigeration systems containing HFC, HCFC, and/or CFC-refrigerants and lubricants used conventionally therewith. Preferably, the present methods involve recharging a refrigerant system that contains a refrigerant to be replaced and a lubricant comprising the steps of (a) removing the refrigerant to be replaced from the refrigeration system while retaining a substantial portion of the lubricant in said system; and (b) introducing to the system a composition of the present invention. As used herein, the term "substantial portion" refers generally to a quantity of lubricant which is at least about 50% (by weight) of the quantity of lubricant contained in the refrigeration system prior to removal of the chlorine-containing refrigerant. Preferably, the substantial portion of lubricant in the system according to the present invention is a quantity of at least about 60% of the lubricant contained originally in the refrigeration system, and more preferably a quantity of at least about 70%. As used herein the term "refrigeration system" refers generally to any system or apparatus, or any part or portion of such a system or apparatus, which employs a refrigerant to provide cooling. Such refrigeration systems include, for example, air conditioners, electric refrigerators, chillers, transport refrigeration systems, commercial refrigeration systems and the like.

Many existing refrigeration systems are currently adapted for use in connection with existing refrigerants, and the compositions of the present invention are believed to be adaptable for use in many of such systems, either with or without system modification. In many applications the compositions of the present invention may provide an advantage as a replacement in smaller systems currently based on certain refrigerants, for example those requiring a small refrigerating capacity and thereby dictating a need for relatively small compressor displacement. Furthermore, in embodiments where it is desired to use a lower capacity refrigerant composition of the present invention, for reasons of efficiency for example, to replace a refrigerant of higher capacity, such embodiments of the present compositions provide a potential advantage. Thus, it is preferred in certain embodiments to use compositions of the present invention, particularly compositions comprising a substantial proportion of, and in some embodiments consisting essentially of the present azeotrope-like compositions, as a replacement for existing refrigerants, such as: HFC-134a; CFC-12; HCFC-22; HFC-152a; combinations of pentfluoroethane (HFC-125), trifluorethane (HFC-1 43a) and tetrafluoroethane (HFC-134a) (the combination HFC-125:HFC-143a:HFC134a in approximate 44:52:4 weight ratio is referred to as R-404A); combinations of HFC-32, HFC-125 and HFC-134a (the combination HFC-32:HFC-125:HFC134a in approximate 23:25:52 weight ratio is referred to as R-407C); combinations of methylene fluoride (HFC-32) and pentfluoroethane (HFC-125) (the combination HFC-32:HFC-125 in approximate 50:50 weight ratio is referred to as R-410A); the combination of CFC-12 and 1,1-difluorethane (HFC-152a) (the combination CFC-12:HFC-152a in a 73.8:26.2 weight ratio is referred to R-500); and combinations of HFC-125 and HFC-143a (the combination HFC-125:HFC143a in approximate 50:50 weight ratio is referred to as R-507A). In certain embodiments it may also be beneficial to use the present compositions in connection with the replacement of referigerants formed from the combination HFC-32:HFC-125:HFC134a in approximate 20:40:40 weight ratio, which is referred to as R-407A, or in approximate 15:15:70 weight ratio, which is referred to as R-407D. Heat transfer compositions of the present invention are particularly preferred as replacements for R-22, R-32, R-404A, R-407A, R-407C, R-407D, R-410A and R-507A. The present compositions are also believed to be suitable as replacements for the above noted compositions in other applications, such as aerosols, blowing agents and the like.

In certain applications, the refrigerants of the present invention potentially permit the beneficial use of larger displacement compressors, thereby resulting in better energy efficiency than other refrigerants, such as HFC-134a. Therefore the refrigerant compositions of the present invention provide the possibility of achieving a competitive advantage on an energy basis for refrigerant replacement applications. It is contemplated that the compositions of the present also have advantage (either in original systems or when used as a replacement for refrigerants such as CFC-12, HCFC-22, HFC-134a, HFC-152a R-404A, R-410A, R-407C, R-500 and R-507A), in chillers typically used in connection with commercial air conditioning and refrigeration systems. In certain of such embodiments it is preferred to including in the present compositions from about 0.5 to about 30%, and in certain cases more preferably 0.5% to about 15% by weight of a supplemental flammability suppressant. In this regard it is noted that the HFO-1234ze component and the other compound in the azeotrope-like compositon of the present compositions may in certain embodiments act as a flammability suppressant with respect to other components in the composition. For example, in cases where other components more flammable than HFO-1234ze are included in the composition, HFO1234-ze may function to suppress the flammability of such other component. Thus, any additional components which have flammability suppressant functionality in the composition will sometimes be referred to herein as a supplemental flammability suppressant.

In certain embodiments, co-refrigerants, including for example HFCs, HCFCs and CFCs may be included in the heat transfer compositions of the present invention, including one or more of the following compounds, including any and all isomers thereof:

Trichlorofluoromethane (CFC-11)

Dichlorodifluoromethane (CFC-12)

Difluoromethane (HFC-32)

1,1,1,3,3,3-hexafluoropropane (HFC-236fa)

1,1,1,3,3-pentafluoropropane (HFC-245fa)

1,1,1,3,3-pentafluorobutane (HFC-365mfc)

water

CO2

The relative amount of any of the above noted components, as well as any additional components which may be included in present compositions, may be incorporated in amounts depending on the particular application for the composition, and all such relative amounts are considered to be within the scope hereof, provided preferably that such components do not negate the azeotrope-like nature of the preferred compositions described herein.

The present methods, systems and compositions are thus adaptable for use in connection with automotive air conditioning systems and devices, commercial refrigeration systems and devices, chillers (including systems which utilize centrifugal compressors), residential refrigerator and freezers, general air conditioning systems, heat pumps, and the like.

Any of a wide range of known methods can be used to remove refrigerants to be replaced from a refrigeration system while removing less than a major portion of the lubricant contained in the system. For example, because refrigerants are quite volatile relative to traditional hydrocarbon-based lubricants (the boiling points of refrigerants are generally less than 10° C. whereas the boiling points of mineral oils are generally more than 200° C.), in embodiments wherein the lubricant is a hydrocarbon-based lubricant, the removal step may readily be performed by pumping chlorine-containing refrigerants in the gaseous state out of a refrigeration system containing liquid state lubricants. Such removal can be achieved in any of a number of ways known in the art, including, the use of a refrigerant recovery system, such as the recovery system manufactured by Robinair of Ohio. Alternatively, a cooled, evacuated refrigerant container can be attached to the low pressure side of a refrigeration system such that the gaseous refrigerant is drawn into the evacuated container and removed. Moreover, a compressor may be attached to a refrigeration system to pump the refrigerant from the system to an evacuated container. In light of the above disclosure, those of ordinary skill in the art will be readily able to remove chlorine-containing lubricants from refrigeration systems and to provide a refrigeration system having therein a hydrocarbon-based lubricant and substantially no chlorine-containing refrigerant according to the present invention.

Any of a wide range of methods for introducing the present refrigerant compositions to a refrigeration system can be used in the present invention. For example, one method comprises attaching a refrigerant container to the low-pressure side of a refrigeration system and turning on the refrigeration system compressor to pull the refrigerant into the system. In such embodiments, the refrigerant container may be placed on a scale such that the amount of refrigerant composition entering the system can be monitored. When a desired amount of refrigerant composition has been introduced into the system, charging is stopped. Alternatively, a wide range of charging tools, known to those of skill in the art, is commercially available. Accordingly, in light of the above disclosure, those of skill in the art will be readily able to introduce the refrigerant compositions of the present invention into refrigeration systems according to the present invention without undue experimentation.

According to certain other embodiments, the present invention provides refrigeration systems comprising a refrigerant of the present invention and methods of producing heating or cooling by condensing and/or evaporating a composition of the present invention. In certain preferred embodiments, the methods for cooling including cooling of other fluid either directly or indirectly or a body directly or indirectly, comprise condensing a refrigerant composition comprising an azeotrope-like composition of the present invention and thereafter evaporating said refrigerant composition in the vicinity of the fluid or body to be cooled. Certain preferred methods for heating an article comprise condensing a refrigerant composition comprising an azeotrope-like composition of the present invention in the vicinity of the fluid or body to be heated and thereafter evaporating said refrigerant composition. As used herein, the term "body" is intended to refer not only to inanimate objects but also to living tissue, including animal tissue in general and human tissue in particular. For example, certain aspects of the present invention involved application of the present composition to human tissue for one or more therapeutic purposes, such as a pain killing technique, as a preparatory anesthetic, or as part of a therapy involving reducing the temperature of the body being treated. In certain embodiments, the application to the body comprises providing the present compositions in liquid form under pressure, preferably in a pressurized container having a one-way discharge valve and/or nozzle, and releasing the liquid from the pressurized container by spraying or otherwise applying the composition to the body. In light of the disclosure herein, those of skill in the art will be readily able to heat and cool articles according to the present inventions without undue experimentation.

Applicants have found that in the systems of the present invention many of the important refrigeration system performance parameters are relatively close to the parameters for R-134a. Since many existing refrigeration systems have been designed for R-134a, or for other refrigerants with properties similar to R-134a, those skilled in the art will appreciate the substantial advantage of a low GWP and/or a low ozone depleting refrigerant that can be used as replacement for R-134a or like refrigerants with relatively minimal modifications to the system. It is contemplated that in certain embodiments the present invention provides retrofitting methods which comprise replacing the refrigerant in an existing system with a composition of the present invention, without substantial modification of the system. In certain preferred embodiments the replacement step is a drop-in replacement in the sense that no substantial redesign of the system is required and no major item of equipment needs to be replaced in order to accommodate the refrigerant of the present invention. In certain preferred embodiments, the methods comprise a drop-in replacement in which the capacity of the system is at least about 70%, preferably at least about 85%, and even more preferably at least about 90% of the system capacity prior to replacement. In certain preferred embodiments, the methods comprise a drop-in replacement in which the suction pressure and/or the discharge pressure of the system, and even more preferably both, is/are at least about 70%, more preferably at least about 90% and even more preferably at least about 95% of the system capacity prior to replacement. In certain preferred embodiments, the methods comprise a drop-in replacement in which the mass flow of the system is at least about 80%, and even more preferably at least 90% of the system capacity prior to replacement.

In another embodiment, the azeotrope-like compositions of this invention may be used as propellants in sprayable compositions, either alone or in combination with known propellants. The propellant composition comprises, more preferably consists essentially of, and, even more preferably, consists of the azeotrope-like compositions of the invention. The active ingredient to be sprayed together with inert ingredients, solvents, and other materials may also be present in the sprayable mixture. Preferably, the sprayable composition is an aerosol. Suitable active materials to be sprayed include, without limitation, cosmetic materials such as deodorants, perfumes, hair sprays, and cleaning solvents, as well as medicinal materials such as anti-asthma medications. The term medicinal materials is used herein in its broadest sense to include any and all materials which are, or at least are believe to be, effective in connection with therapeutic, diagnostic, pain relief, and similar treatments, and as such would include for example drugs and biologically active substances.

Yet another embodiment of the present invention relates to a blowing agent comprising one or more azeotrope-like compositions of the invention. In general, the blowing agent may include the azeotrope-like compositions of the present invention in widely ranging amounts. It is generally preferred, however, that the blowing agents comprise the present azeotrope-like compositions in amounts at least about 5% by weight, and even more preferably at least about 15% by weight, of the blowing agent. In certain preferred embodiments, the blowing agent comprises at least about 50% by weight of the present compositions, and in certain embodiments the blowing agent consists essentially of the present azeotrope-like composition. In certain preferred embodiments, the blowing agent includes, in addition to the present compositions, one or more of co-blowing agents, fillers, vapor pressure modifiers, flame suppressants, stabilizers and like adjuvants.

In other embodiments, the invention provides foamable compositions. The foamable compositions of the present invention generally include one or more components capable of forming foam having a generally cellular structure and a blowing agent in accordance with the present invention. In certain embodiments, the one or more components comprise a thermosetting composition capable of forming foam and/or foamable compositions. Examples of thermosetting compositions include polyurethane and polyisocyanurate foam compositions, and also phenolic foam compositions and methods of preparing foams. In such thermosetting foam embodiments, one or more of the present azeotrope-like compositions are included as a blowing agent in a foamable composition, or as a part of a two or more part foamable composition, which composition preferably includes one or more additional components capable of reacting and foaming under the proper conditions to form a foam or cellular structure, as is well known in the art. In certain other embodiments, the one or more components comprise thermoplastic materials, particularly thermoplastic polymers and/or resins. Examples of thermoplastic foam components include polyolefins, such as polystyrene (PS), polyethylene (PE), polypropylene (PP) and polyethyleneterepthalate (PET), and foams formed therefrom, preferably low-density foams. In certain embodiments, the thermoplastic foamable composition is an extrudable composition.

It will be appreciated by those skilled in the art, especially in view of the disclosure contained herein, that the order and manner in which the blowing agent of the present invention is formed and/or added to the foamable composition does not generally affect the operability of the present invention. For example, in the case of extrudable foams, it is possible that the various components of the blowing agent, and even the components of the present composition, be not be mixed in advance of introduction to the extrusion equipment, or even that the components are not added to the same location in the extrusion equipment. Thus, in certain embodiments it may be desired to introduce one or more components of the blowing agent at first location in the extruder, which is upstream of the place of addition of one or more other components of the blowing agent, with the expectation that the components will come together in the extruder and/or operate more effectively in this manner. Nevertheless, in certain embodiments, two or more components of the blowing agent are combined in advance and introduced together into the foamable composition, either directly or as part of premix which is then further added to other parts of the foamable composition.

The invention also relates to foam, and preferably closed cell foam, prepared from a polymer foam formulation containing a composition of the invention, preferably as part of blowing agent.

In certain preferred embodiments, dispersing agents, cell stabilizers, surfactants and other additives may also be incorporated into the blowing agent compositions of the present invention. Surfactants are optionally but preferably added to serve as cell stabilizers. Some representative materials are sold under the names of DC-193, B-8404, and L-5340 which are, generally, polysiloxane polyoxyalkylene block co-polymers such as those disclosed in U.S. Pat. Nos. 2,834,748, 2,917,480, and 2,846,458, each of which is incorporated herein by reference. Other optional additives for the blowing agent mixture may include flame retardants or suppressants such as tri(2-chloroethyl)phosphate, tri(2-chloropropyl) phosphate, tri(2,3-dibromopropyl)-phosphate, tri(1,3-dichloropropyl) phosphate, diammonium phosphate, various halogenated aromatic compounds, antimony oxide, aluminum trihydrate, polyvinyl chloride, and the like.

Any of the methods well known in the art, such as those described in “Polyurethanes Chemistry and Technology,” Volumes I and II, Saunders and Frisch, 1962, John Wiley and Sons, New York, N.Y., which is incorporated herein by reference, may be used or adapted for use in accordance with the foam embodiments of the present invention.

Other uses of the present azeotrope-like compositions include use as solvents, cleaning agents, and the like. Those of skill in the art will be readily able to adapt the present compositions for use in such applications without undue experimentation.

EXAMPLES

The invention is further illustrated in the following example which is intended to be illustrative, but not limiting in any manner. For examples 1-4, a ebulliometer of the general type described by Swietolslowski in his book "Ebulliometric Measurements" (Reinhold, 1945) was used.

Example 1

An ebulliometer consisting of vacuum jacketed tube with a condenser on top which is further equipped with a Quartz Thermometer is used. About 21 g HFC-134a is charged to the ebulliometer and then HFO-1234ze is added in small, measured increments. Temperature depression is observed when HFO-1234 is added to HFC-134a, indicating a binary minimum boiling azeotrope is formed. From greater than about 0 to about 51 weight percent HFO-1234ze, the boiling point of the composition changed by about 1.3° C. or less. The binary mixtures shown in Table 1 were studied and the boiling point of the compositions changed by less than about 2° C. The compositions exhibit azeotrope and/or azeotrope-like properties over this range.

TABLE 1

HFO-1234/HFC-134a compositions at 14.41 psia

| T (C.) | Wt. % 134a | Wt. % Trans-1234ze |
|---|---|---|
| −25.288 | 100.00 | 0.00 |
| −25.522 | 99.07 | 0.93 |
| −25.581 | 95.01 | 4.99 |
| −25.513 | 91.74 | 8.26 |
| −25.444 | 86.21 | 13.79 |
| −25.366 | 77.87 | 22.13 |
| −24.926 | 67.47 | 32.53 |
| −24.633 | 61.67 | 38.33 |
| −24.291 | 55.23 | 44.77 |
| −23.998 | 51.05 | 48.95 |

Example 2

An ebulliometer consisting of vacuum jacketed tube with a condenser on top which is further equipped with a Quartz Thermometer is used. About 35 g HFC-125 is charged to the ebulliometer and then HFO-1234ze is added in small, measured increments. Temperature depression is observed when HFO-1234ze is added to HFC-125, indicating a binary minimum boiling azeotrope is formed. From greater than about 0 to about 24 weight percent HFO-1234ze, the boiling point of the composition changed by about 2° C. or less. The binary mixtures shown in Table 1 were studied and the boiling point of the compositions changed by less than about 6° C. The compositions exhibit azeotrope and/or azeotrope-like properties over this range.

TABLE 2

HFO-1234/HFC-125 compositions at 14.40 psia

| T (C.) | Wt. % 125 | Wt. % Trans-1234ze |
|---|---|---|
| −48.446 | 100.00 | 0.00 |
| −48.546 | 99.42 | 0.58 |
| −48.898 | 96.35 | 3.65 |
| −48.697 | 92.27 | 7.73 |
| −47.842 | 84.68 | 15.32 |
| −46.686 | 77.49 | 22.51 |
| −44.856 | 68.02 | 31.98 |
| −43.177 | 59.57 | 40.43 |
| −42.513 | 56.97 | 43.03 |

Example 3

An ebulliometer consisting of vacuum jacketed tube with a condenser on top which is further equipped with a Quartz Thermometer is used. About 17 g HFC-152a is charged to the ebulliometer and then HFO-1234 is added in small, measured increments. Temperature depression is observed when HFO-1234 is added to HFC-152a, indicating a binary minimum boiling azeotrope is formed. From greater than about 0 to about 30 weight percent HFO-1234, the boiling point of the composition changed by about 0.8° C. or less. The binary mixtures shown in Table 1 were studied and the boiling point of the compositions changed by less than about 1° C. The compositions exhibit azeotrope and/or azeotrope-like properties over this range.

TABLE 3

HFO-1234/HFC-152a compositions at 14.39 psia

| T (C.) | Wt. % 152a | Wt. % Trans-1234ze |
|---|---|---|
| −23.455 | 100.00 | 0.00 |
| −23.504 | 99.34 | 0.66 |
| −23.631 | 96.83 | 3.17 |
| −23.778 | 94.99 | 5.01 |
| −23.817 | 87.22 | 12.78 |
| −24.160 | 81.49 | 18.51 |
| −23.797 | 70.59 | 29.41 |

Example 4

An ebulliometer consisting of vacuum jacketed tube with a condenser on top which is further equipped with a Quartz Thermometer is used. About 18 g HFO-1234 is charged to the ebulliometer and then HFC-227ea is added in small, measured increments. Temperature depression is observed when HFC-227ea is added to HFO-1234, indicating a binary minimum boiling azeotrope is formed. From greater than about 0 to about 53 weight percent HFC-227ea, the boiling point of the composition changed by about 0.7° C. or less. The binary mixtures shown in Table 1 were studied and the boiling point of the compositions changed by less than about 1° C. The compositions exhibit azeotrope and/or azeotrope-like properties over this range.

TABLE 4

| HFO-1234/HFC-227ea compositions at 14.44 psia | | |
|---|---|---|
| T (C.) | Wt. % Trans-1234ze | Wt. % 227ea |
| −18.124 | 100.00 | 0.00 |
| −18.310 | 98.87 | 1.13 |
| −18.506 | 93.23 | 6.77 |
| −18.653 | 86.62 | 13.38 |
| −18.741 | 76.24 | 23.76 |
| −18.555 | 66.40 | 33.60 |
| −18.359 | 58.18 | 41.82 |
| −18.114 | 52.63 | 47.37 |
| −18.055 | 46.56 | 53.44 |

What is claimed is:

1. A foamable composition comprising one or more components capable of forming foam and an azeotrope-like composition consisting of trans-1,3,3,3-tetrafluoropropene (transHFO-1234ze) and a component selected from the group consisting of 1,1-difluoroethane ("HFC-152a"), 1,1,1,2,3,3,3-heptafluoropropane ("HFC-227ea"), 1,1,1,2-tetrafluoroethane ("HFC-134a"), 1,1,1,2,2-pentafluoroethane ("HFC-125") and combinations of two or more of these.

2. The foamable composition of claim 1 wherein said azeotrope-like composition consists of from greater than zero to about 75 weight percent transHFO-1234ze and from about 25 to less than 100 weight percent of HFC-134a.

3. The foamable composition of claim 1 wherein said azeotrope-like composition consists of from greater than zero to about 60 weight percent transHFO-1234ze and from about 40 to less than 100 weight percent of HFC-134a.

4. The foamable composition of claim 1 wherein said azeotrope-like composition consists of from about 1 to about 40 weight percent transHFO-1234ze and from about 60 to about 99 weight percent of HFC-134a.

5. The foamable composition of claim 1 wherein said azeotrope-like composition consists of from about 5 to about 35 weight percent transHFO-1234ze and from about 65 to about 95 weight percent of HFC-134a.

6. The foamable composition of claim 1 wherein said azeotrope-like composition has a boiling point of from about −26° C. to about −23° C. at a pressure of about 14.4 psia.

7. The foamable composition of claim 1 wherein said azeotrope-like composition consists of from greater than zero to about 75 weight percent transHFO-1234ze and from about 25 to less than 100 weight percent of HFC-152a.

8. The foamable composition of claim 1 wherein said azeotrope-like composition consists of from greater than zero to about 50 weight percent transHFO-1234ze and from about 50 to less than 100 weight percent of HFC-152a.

9. The foamable composition of claim 1 wherein said azeotrope-like composition consists of from about 15 to about 30 weight percent transHFO-1234ze and from about 70 to about 85 weight percent of HFC-152a.

10. The foamable composition of claim 1 wherein said azeotrope-like composition has a boiling point of from about −26° C. to about −23° C. at a pressure of about 14.4 psia.

11. The foamable composition of claim 1 wherein said azeotrope-like composition consists of from greater than zero to about 75 weight percent transHFO-1234ze and from about 25 to less than 100 weight percent of HFC-125.

12. The foamable composition of claim 1 wherein said azeotrope-like composition consists of from greater than zero to about 75 weight percent HFC-227ea and from about 25 to less than 100 weight percent of transHFO-1234ze.

13. The foamable composition of claim 1 wherein said one or more components capable of forming a foam comprise at least one component selected from the group consisting of thermoplastic foams, polystyrene foams, polyethylene foams, low density polyethylene foams, extruded thermoplastic foams, polyurethane foams, and polyisocyanurate foams.

14. The foamable composition of claim 13 farther comprising at least one additive selected from the group consisting of dispersing agents, cell stabilizers, surfactants, flame retardants, and combinations of two or more of these.

15. A foam formed from the foamable composition of claim 1.

16. A closed cell foam having a cell gas comprising an azeotrope-like composition consisting of trans-1,3,3,3-tetrafluoropropene (transHFO-1234ze) and a component selected from the group consisting of 1,1-difluoroethane ("HFC-152a"), 1,1,1,2,3,3,3-heptafluoropropane ("HFC-227ea"), 1,1,1,2-tetrafluoroethane ("HFC-134a"), 1,1,1,2,2-pentafluoroethane ("HFC-125") and combinations of two or more of these.

17. The closed cell foam of claim 16 wherein said azeotrope-like composition consists of from greater than zero to about 75 weight percent transHFO-1234ze and from about 25 to less than 100 weight percent of HFC-134a.

18. The closed cell foam of claim 16 wherein said azeotrope-like composition consists of from greater than zero to about 60 weight percent transHFO-1234ze and from about 40 to less than 100 weight percent of HFC-134a.

19. The closed cell foam of claim 16 wherein said azeotrope-like composition consists of from about 1 to about 40 weight percent transHFO-1234ze and from about 60 to about 99 weight percent of HFC-134a.

20. The closed cell foam of claim 16 wherein said azeotrope-like composition consists of from about 5 to about 35 weight percent transHFO-1234ze and from about 65 to about 95 weight percent of HFC-134a.

21. The closed cell foam of claim 16 wherein said azeotrope-like composition has a boiling point of from about −26° C. to about −23° C. at a pressure of about 14.4 psia.

22. The closed cell foam of claim 16 wherein said azeotrope-like composition consists of from greater than zero to about 75 weight percent transHFO-1234ze and from about 25 to less than 100 weight percent of HFC-152a.

23. The closed cell foam of claim 16 wherein said azeotrope-like composition consists of from greater than zero to about 50 weight percent transHFO-1234ze and from about 50 to less than 100 weight percent of HFC-152a.

24. The closed cell foam of claim 16 wherein said azeotrope-like composition consists of from about 15 to about 30 weight percent transHFO-1234ze and from about 70 to about 85 weight percent of HFC-152a.

25. The closed cell foam of claim 16 wherein said azeotrope-like composition has a boiling point of from about −26° C. to about −23° C. at a pressure of about 14.4 psia.

26. The closed cell foam of claim 16 wherein said azeotrope-like composition consists of from greater than zero to about 75 weight percent transHFO-1234ze and from about 25 to less than 100 weight percent of HFC-125.

27. The closed cell foam of claim 16 wherein said azeotrope-like composition consists of from greater than zero to about 75 weight percent HFC-227ea and from about 25 to less than 100 weight percent of transHFO-1234ze.

* * * * *